US006748257B2

(12) United States Patent
Ozaki (10) Patent No.: US 6,748,257 B2
(45) Date of Patent: Jun. 8, 2004

(54) DETECTION OF RIBCAGE BOUNDARY FROM DIGITAL CHEST IMAGE

(75) Inventor: Osamu Ozaki, Amagasaki (JP)

(73) Assignee: Mitsubishi Space Software Co., Ltd., Tokyo (JP)

( * ) Notice: Subject to any disclaimer, the term of this patent is extended or adjusted under 35 U.S.C. 154(b) by 147 days.

(21) Appl. No.: 09/983,613

(22) Filed: Oct. 25, 2001

(65) Prior Publication Data

US 2002/0072665 A1 Jun. 13, 2002

(30) Foreign Application Priority Data

Dec. 13, 2000 (JP) ........................................ 2000-378753

(51) Int. Cl.[7] ................................................ A61B 5/05
(52) U.S. Cl. ........................ 600/408; 128/920; 128/922; 128/925; 382/131; 382/132; 382/199; 382/266
(58) Field of Search ................................. 600/407, 408; 128/920, 922, 925, 898; 382/128, 130, 131, 132, 199, 266, 273; 378/21, 901

(56) References Cited

U.S. PATENT DOCUMENTS 5,343,390 A * 8/1994 Doi et al. .................... 382/132
5,790,690 A 8/1998 Doi et al.
5,974,165 A * 10/1999 Giger et al. ................. 382/132
5,982,915 A * 11/1999 Doi et al. .................... 382/130

FOREIGN PATENT DOCUMENTS

JP 7-037074 2/1995
JP 8-335271 12/1996

* cited by examiner

Primary Examiner—Eleni Mantis Mercader
(74) Attorney, Agent, or Firm—Wenderoth, Lind & Ponack, L.L.P.

(57) ABSTRACT

To prevent erroneous detection of a ribcage boundary from a chest image, an outer search limit point is decided with precision. A profile of smoothed pixel-value integrated averages in each of right and left lung field of the image is obtained, a threshold for each of the right and left lung fields with the profile taken as a reference is decided, and each of the right and left lung fields is searched from a central part of each lung field outwardly on the image so that a position exceeding the threshold is determined. The position is set as the outer search limit point for a series of a upper lung ribcage boundary candidate points. In the search, in cases the position exceeding the threshold is not found, a first derivative of the profile is used to decide the outer search limit point.

4 Claims, 11 Drawing Sheets

FIG.1

PRIOR ART

FIG.2

PRIOR ART

DETECTION OF RIBCAGE BOUNDARY FROM DIGITAL CHEST IMAGE

BACKGROUND OF THE INVENTION

The present invention relates to an image processing technique for automatically and accurately detecting an anatomical configuration from a chest image necessary for computer-aided diagnosis of the chest, and in particular, to an image processing technique that makes it possible to detect a boundary of a ribcage from a chest image with higher precision, even when its image is poor in quality.

Digitized chest radiographs have been used widely in the field of computer-aided diagnosis. There have been known a wide variety of types of computer-aided diagnosis capable of automatically detecting ribcage boundary information and landmark information both specifying anatomical configurations of the chest. One conventional technique is provided by "Xin-Wei Xu and Kunio Doi, Image feature analysis for computer-aided diagnosis: Accurate determination of ribcage boundary in chest radiographs, Med. Phys. 22(5), May 1995." This technique is also provided by Japanese Patent Laid-open Publication NO.7-37074.

This diagnostic technique uses lesion-enhanced images in order to detect temporal changes of diseases such as lung diseases among digital chest images acquired at different times for the same patient's region. To raise diagnostic accuracy, this technique comprises the steps of obtaining previous and current digital chest images, positioning both previous and current digital images by performing non-linear warping processing based on a non-linear warping technique on either the first or second digital image, and making a subtraction between previous and current images one of which (has undergone the non-linear warping. The non-linear warping technique uses information detected from a chest image in relation to its anatomical structure and is based on a local matching technique to be applied to a number of tiny regions of interest (ROIs) selected on the basis of the information. The non-linear warping technique is mapping of amounts of matching shift obtained between corresponding locations in two frames of images. The mapping is realized using amounts of local matching resulting from a local matching technique applied to the locations and a weighted fitting technique that uses weighting coefficients resulting from image data analysis applied to the ROIs. In addition, the mapping of shift amounts is based on two-dimensional polynomial functions fitted to shift values.

Figure 1:
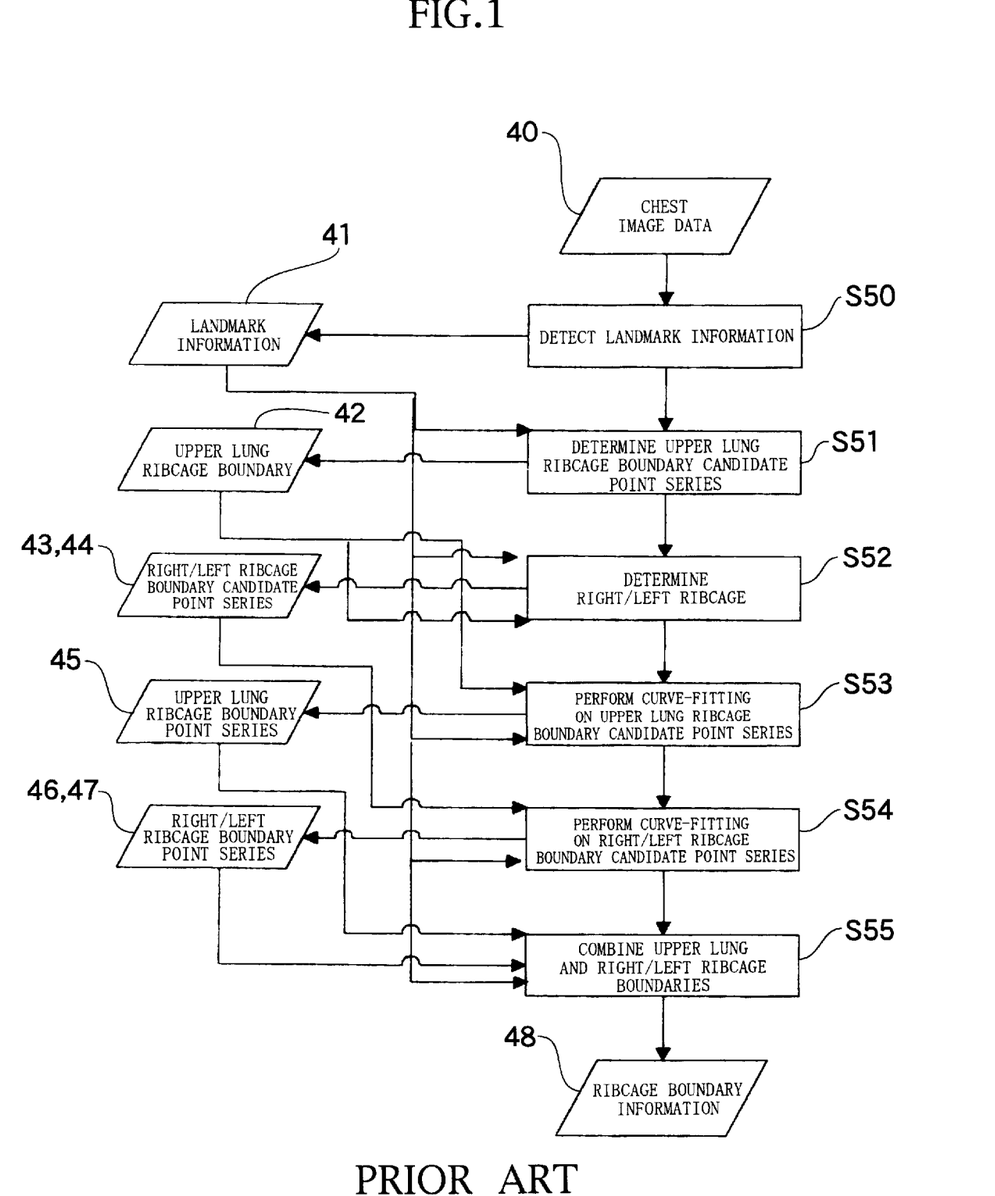
FIG. 1 is a flowchart showing a conventionally used technique for acquiring ribcage boundary information.

The above conventional automatic detection technique provides a ribcage boundary in the procedures detailed in FIG. 1.

First, as pre-processing for detecting a ribcage boundary from chest image data 40, information indicative of landmarks 41, which becomes landmark information in displaying a configuration of the chest (Step S50).

Then, based on the landmark information 41, a series of upper lung ribcage boundary candidate points is detected (Step S51). Based on both landmark information 41 and upper lung ribcage boundary candidate point series 42, a series 43 of right ribcage boundary candidate points and a series 44 of left ribcage boundary candidate points are both detected (Step S52).

Based on the landmark information 41, the upper lung ribcage boundary candidate point series 42 is approximated with polynomials, so that an upper lung ribcage boundary point series 45 consisting of a series of points continuously aligned in the X-coordinate direction (horizontal direction) (Step S53). Like this, based on the landmark information 41, both right and left ribcage boundary candidate point series 43 and 44 are approximated with polynomials, so that right and left ribcage boundary point series 46 and 47 each consisting of a series of points continuously aligned in the Y-coordinate direction (vertical direction) (Step S54).

Finally, on the basis of the landmark information 41, both upper lung ribcage boundary point series 45 and right ribcage boundary point series 46 are combined to obtain a right ribcage boundary, and both upper ribcage boundary point series 45 and left ribcage boundary point series 47 are combined to obtain a left ribcage boundary 48 (Step S55).

This conventional technique adopts the lung length of ⅕ as the landmark information 41 for obtaining the upper lung ribcage boundary point series 45.

Figure 2:
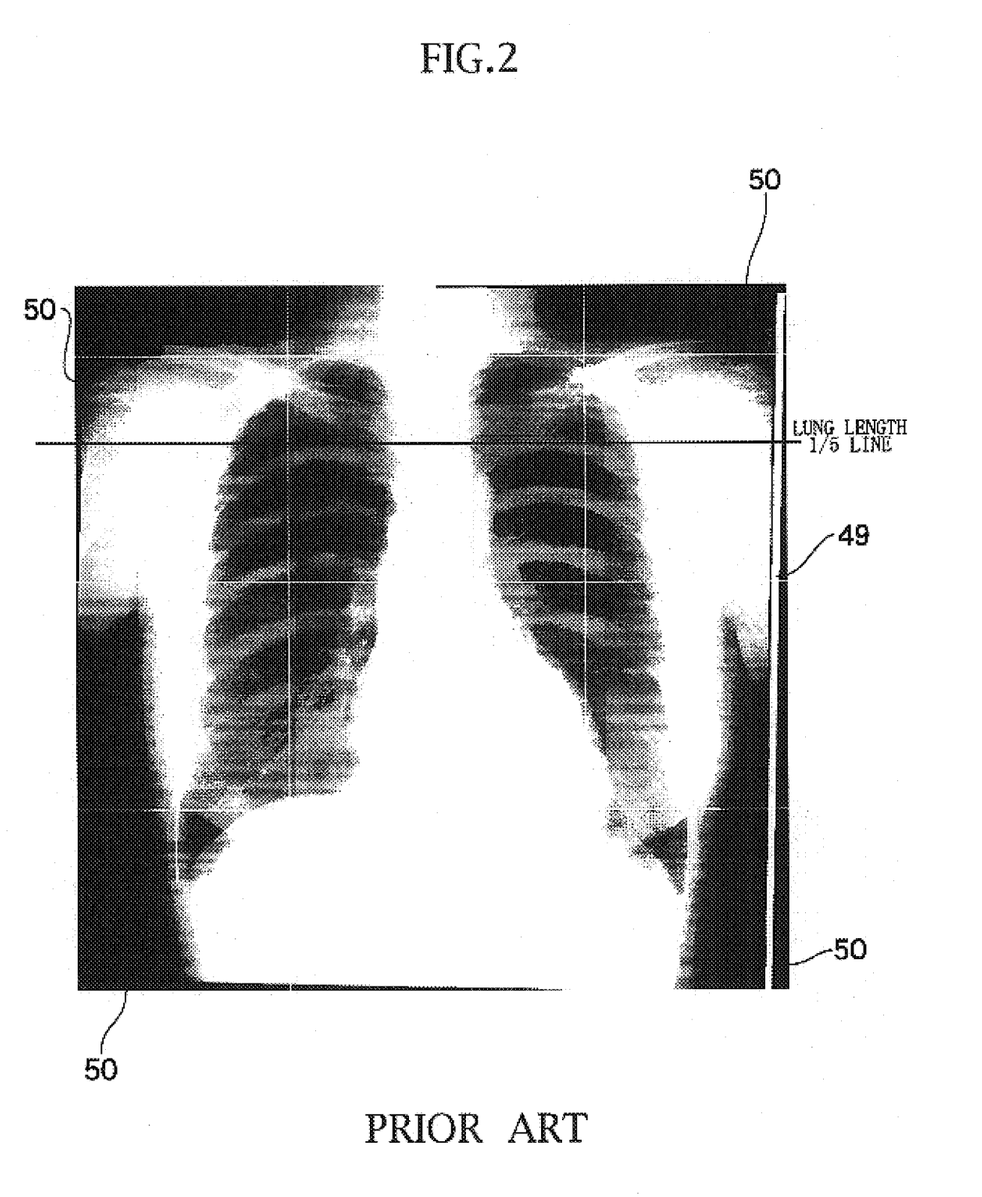
FIG. 2 exemplifies a chest image showing a digital image converted from a chest radiograph using a film digitizer.

However, as shown in FIG. 2, a region along the lung length of ⅕ within the lung field is relatively low in contrast and the original chest image includes artifacts, such as a blank 49 occurring in converting a chest image into a digital image by the use of a film digitizer and noises 50 occurring in image processing. Thus, in some occasions, the foregoing conventional technique fails in detecting search limit points to search a series of ribcage boundary candidate points.

Figure 3A:
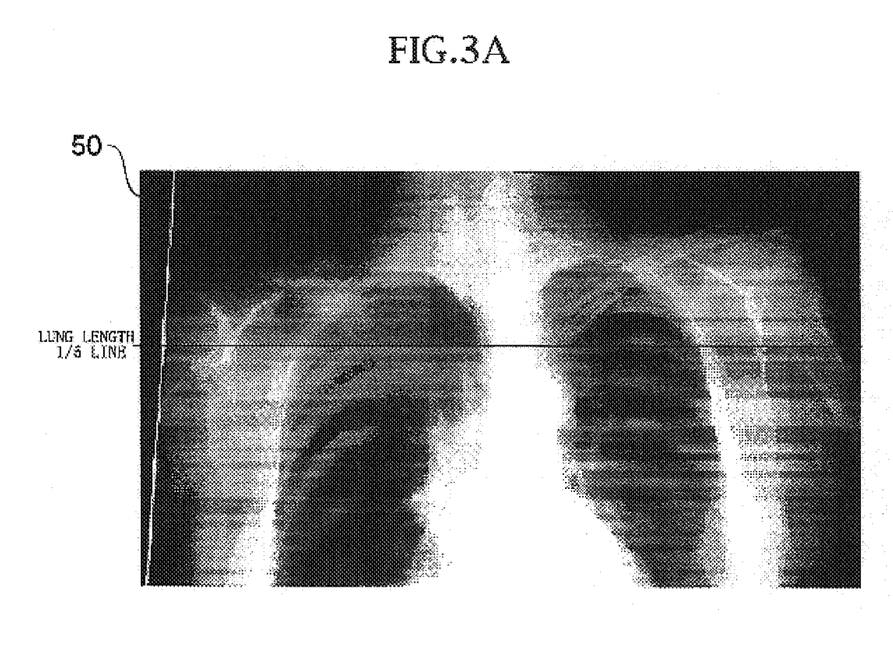
FIG. 3A exemplifies a portion of an original chest image to be detected by the conventional detection technique.
Figure 3B:
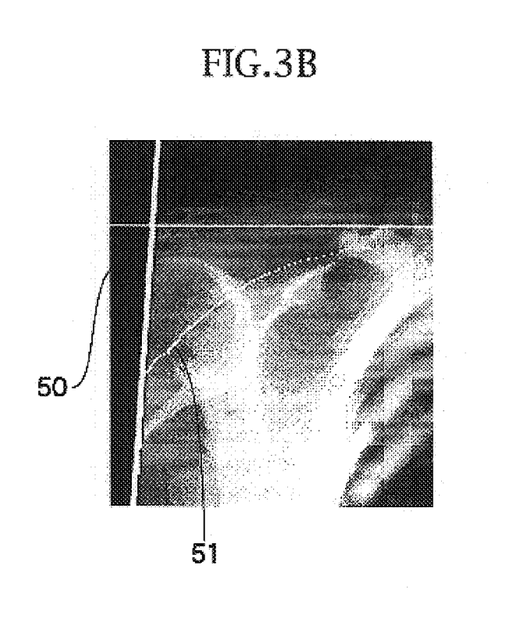
FIG. 3B exemplifies a ribcage boundary erroneously detected by the conventional detection technique.

FIGS. 3A and 3B pictorially show examples in which the detection fails. In the case of FIG. 3A, an artifact that consists of a noise 50 existing at the right side of a chest image has influence on setting an outer search limit point in such a way that a blade bone portion is set as the outer search limit point by mistake. As a result, as shown in FIG. 3B, the processing fails in detecting a series 51 of upper lung right ribcage boundary candidate points.

Specifically, in the case of the conventional detection technique, a fail in detection of ribcage boundary candidate points due to influence of setting a reference for detecting the ribcage boundary candidate points and artifacts on an original chest image results in that a ribcage boundary obtained by approximating polynomials to a series of the ribcage boundary candidate points deviates from the true ribcage boundary, thereby lowering accuracy in computer-aided diagnosis as a whole.

In addition, both right and left ribcage boundary candidate point series are detected from the series of upper lung ribcage boundary candidate points. Hence, failing in detecting the series of upper lung ribcage boundary candidate points will give rise to failure in successively performed detection of both series of right and left ribcage boundary candidate points. A ribcage boundary computed by approximating polynomials to such erroneous ribcage boundary candidate point series is no longer the true ribcage boundary. This will lead to lowered accuracy in computer-aided diagnosis.

For using in computer-aided diagnosis features of a chest image and positional information indicative of an anatomical structure, it is significant to acquire more accurate information about a ribcage boundary and landmarks. It has therefore been strongly desired that the more accurate information be available for computer-aided diagnosis.

SUMMARY OF THE INVENTION

An object of the present invention is to prevent erroneous detection of a ribcage boundary, which was seen in the conventional technique, thereby acquiring accurate ribcage boundary information that will not be influenced by quality of chest images.

In order to realize the above object, one aspect of the present invention is provided by a method for detecting a ribcage boundary for computer-aided diagnosis requiring anatomical structure information to be detected from a digital chest image. The method comprises the steps of obtaining a profile of smoothed pixel-value integrated averages in each of right and left lung field of the image; deciding a threshold for each of the right and left lung fields with the profile taken as a reference; and searching each of the right and left lung fields from a central part of each lung field outwardly on the chest image so as to determine a position exceeding the threshold, the position being set as an outer search limit point for a series of an upper lung ribcage boundary candidate points for the ribcage boundary.

Preferably, the searching step further includes the steps of calculating a first derivative of the profile for examining changes in pixel value within each of the right and left lung fields in cases the position exceeding the threshold is not found; searching not only a position from the central part of each of the right and left lung fields outwardly on the chest image within a predetermined search range, the position showing a maximum change in the first derivative, but also a position showing a maximal value in the profile within the search range; and deciding a median between the maximal value and the position showing the maximum change in the first derivative as the outer search limit point.

By performing this method, the outer search limit point can be determined with a higher precision, preventing a ribcage boundary from being detected erroneously.

According to the present invention, as another mode, there is provided a method for detecting a ribcage boundary for computer-aided diagnosis requiring anatomical structure information to be detected from a digital chest image, comprising the steps of setting a central position in each of right and left lung fields on the chest image, the central position being in the vicinity of a lung length of ½, the central position in each field being symmetric right and left with regard to a midline regarded as a symmetric axis; and deciding a search starting point for each of series of right and left ribcage boundary candidate points from a central position of each of the right and left lung fields outwardly on the chest image.

Using this method, the search starting point for the right and left ribcage boundary candidate point series can be detected with precision even when a series of upper lung ribcage boundary candidate points was erroneously detected. This prevents a ribcage boundary from being detected with errors.

It is preferred that the deciding step includes a step of performing pre-processing for removing an artifact including at least one of a blank arising during a conversion into the digital chest image by use of a film digitizer and a noise (black or white noise) caused by image processing performed on the chest image. Thanks to the pre-processing, the detection of the search starting point will be free from various influences of the artifacts. Hence it is possible to provide information about a ribcage boundary with a more precision, which is independent on quality of chest images.

According to the present invention, another aspect, there is a system for detecting a ribcage boundary for computer-aided diagnosis requiring anatomical structure information to be detected from a digital chest image, comprising a unit for obtaining a profile of smoothed pixel-value integrated averages in each of right and left lung fields of the image, a unit for deciding a threshold for each of the right and left lung fields with the profile taken as a reference, and a unit for searching each of the right and left lung fields from a central part of each lung field outwardly on the chest image so as to determine a position exceeding the threshold, the position being set as an outer search limit point for a series of an upper lung ribcage boundary candidate points. This configuration also enables the outer search limit point to be determined with a higher precision, preventing a ribcage boundary from being detected erroneously.

Figure 4:
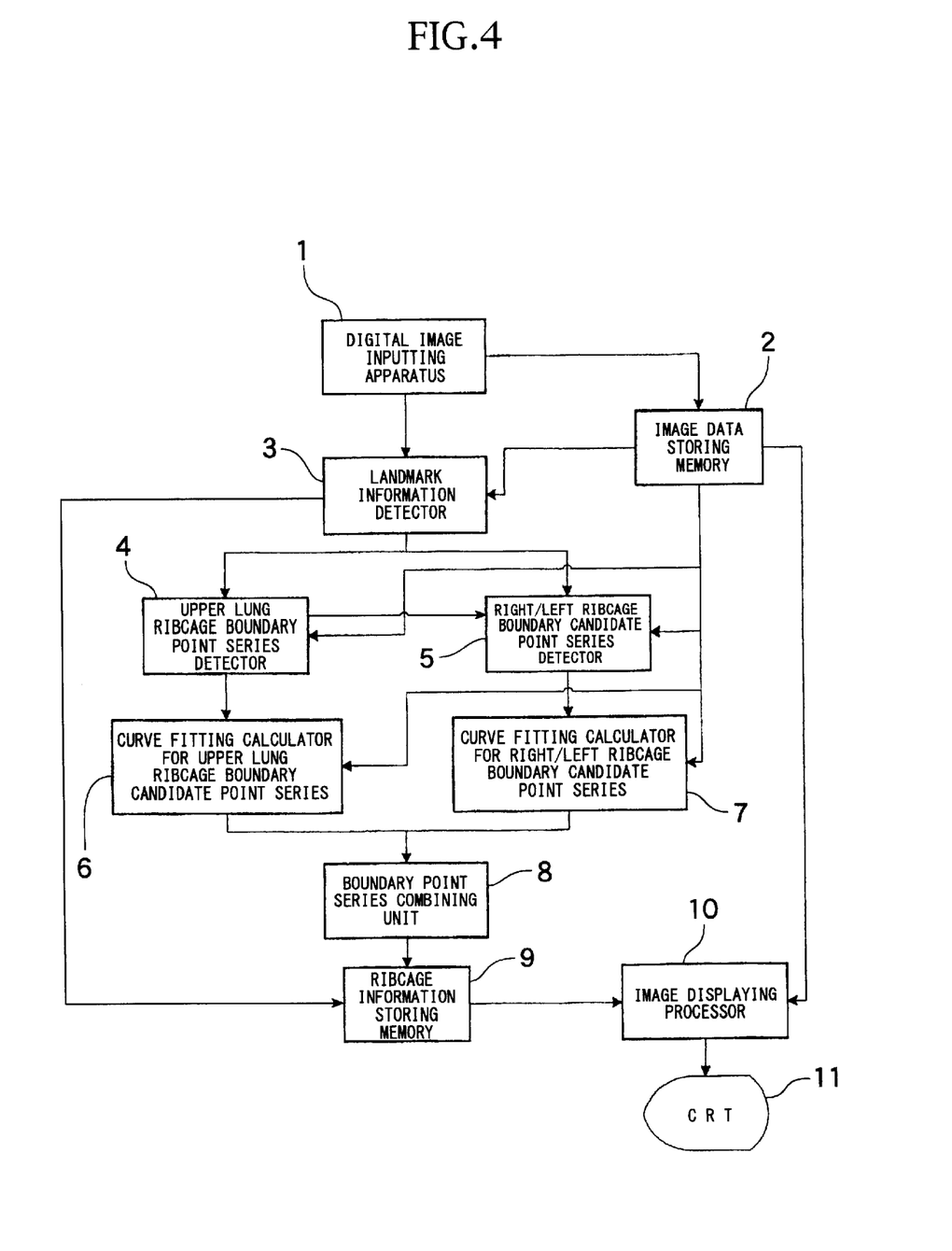
FIG. 4 is a block diagram showing an entire configuration of an image processing system used for detecting a ribcage boundary of a digital chest image according to an embodiment of the present invention.

In the image processing system of FIG. 4, there is provided a digital image inputting apparatus 1 capable of digitizing chest radiographs that were imaged. For digitizing a chest radiograph into a chest image chest image), the digital image inputting apparatus 1 serves as an apparatus such as a film digitizer for digitizing a film. For imaging a chest radiograph in digital, the digital image inputting apparatus 1 operates as a digital imaging system such as a CR (computed radiography) system. Either system can be used, provided that it is able to digitize chest films.

PREFERRED EMBODIMENT OF THE INVENTION

Referring to the accompanying drawings, a preferred embodiment of the present invention will now be described.

Figure 5:
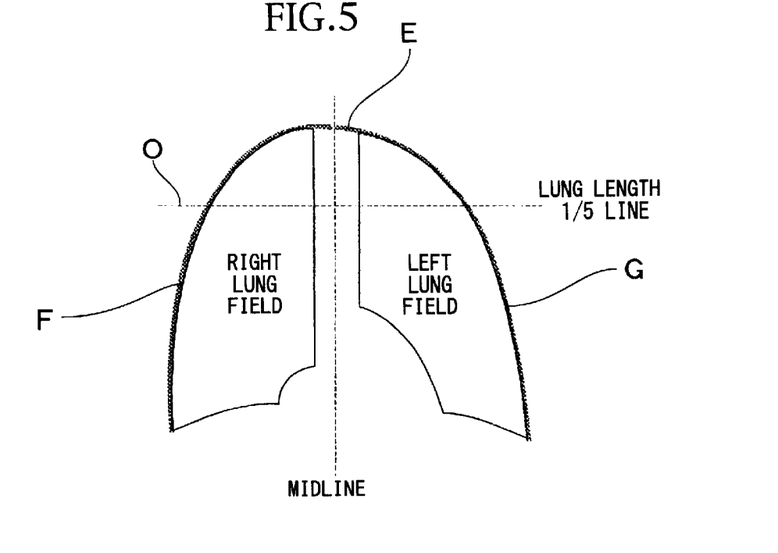
FIG. 5 is an illustration of ribcage information treated as anatomical structure information of a chest image.
Figure 6:
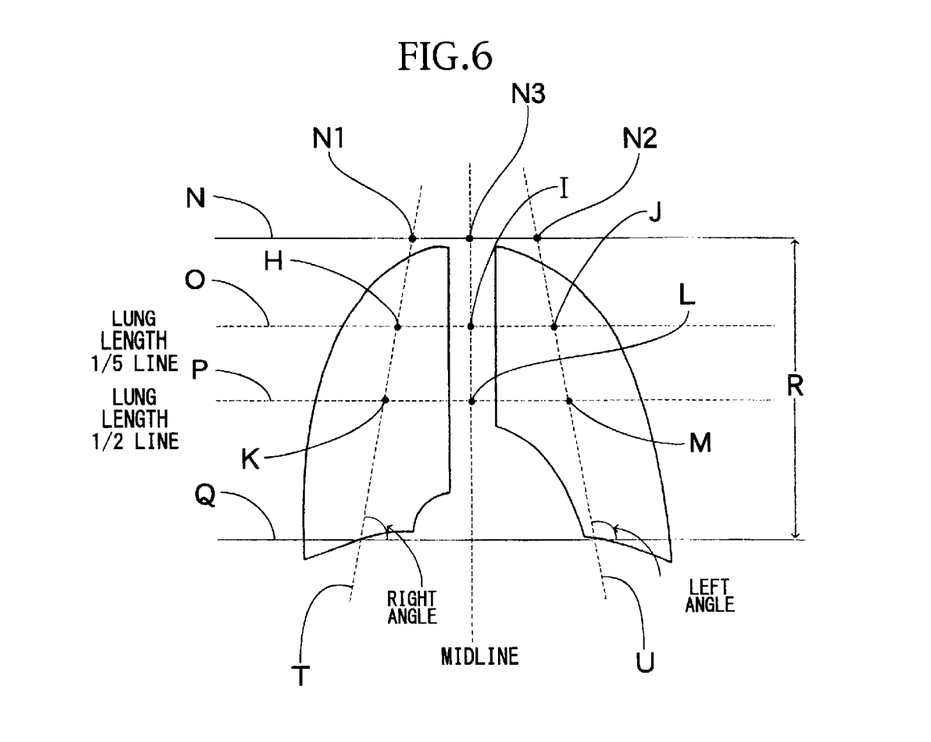
FIG. 6 is an illustration of landmark information composing part of the ribcage information.
Figure 7:
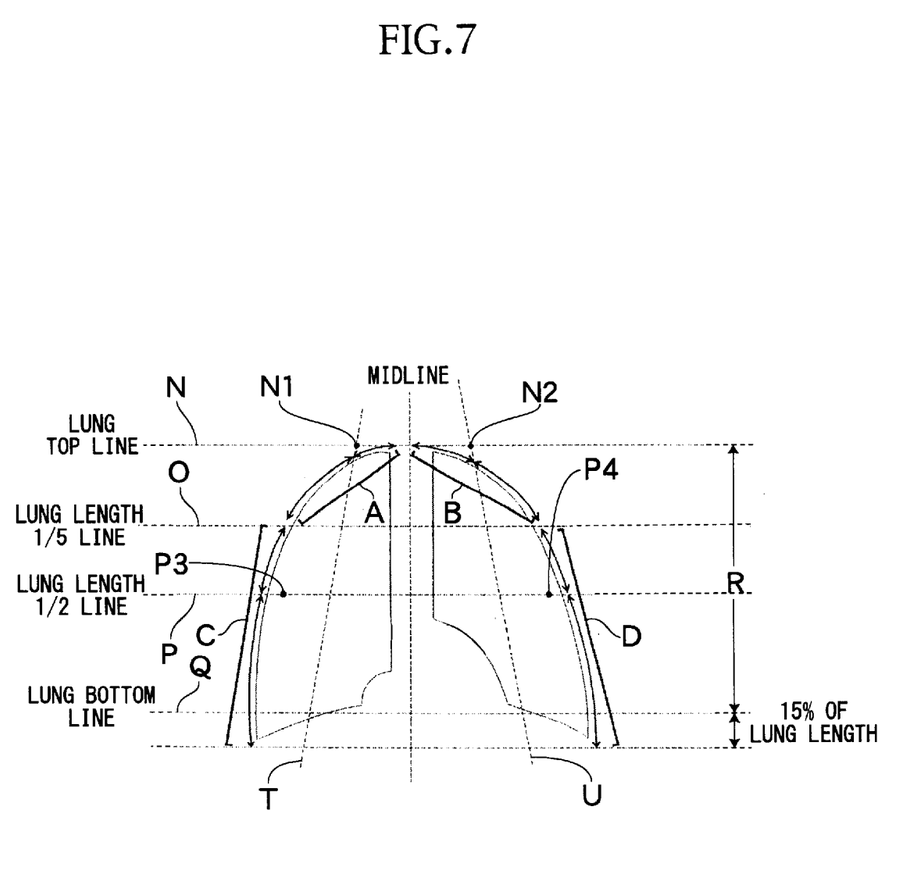
FIG. 7 illustrates series of boundary candidate points adopted as ribcage boundary information composing part of the ribcage information.

FIG. 4 shows the entire configuration of an image processing system according to an embodiment of the present invention, which is used for detecting the boundary of a ribcage from a digital chest image. FIG. 5 illustrates pieces of ribcage information adopted as anatomical structure information of a chest image. FIG. 6 illustrates pieces of landmark information that composes part of the pieces of ribcage information. FIG. 7 illustrates series of boundary candidate points serving as pieces of ribcage boundary information which compose part of the pieces of ribcage information.

As shown in those figures, the ribcage information of a chest image consists of pieces of ribcage boundary information depicting contour lines connecting outer ends of the chest ribs and pieces of landmark information taken as landmarks for displaying a chest configuration.

As shown in FIG. 5, the ribcage boundary information is made up of an upper lung ribcage boundary E that connects series of upper lung ribcage boundary points positioned higher than a lung length 1/5 line, a right ribcage boundary F that connects lines of right ribcage points positioned lower than the lung length 1/5 line, and a left ribcage boundary G that connects lines of left ribcage points positioned lower than the lung length 1/5 line.

As shown in FIG. 6, the landmark information includes coordinates showing positions, such as a center H of the right on the lung length 1/5 line, an X-coordinate I of a midline on the lung length 1/5 line, a center J of the left on the lung length 1/5 line, a center K of the right on the lung length 1/2 line, an X-coordinate L of a midline on the lung length 1/2 line, and a center M of the left on the lung length 1/2 line; Y-coordinates, such as lung top line N of the lung, lung length 1/5 line O, lung length 1/2 line P, lung bottom line Q of the lung; and lengths such as a lung length R.

As shown in FIG. 7, the series of the boundary candidate points, which serve as the ribcage boundary information, include a series A of upper lung right ribcage boundary candidate points, a series B of upper lung left ribcage boundary candidate points, a series C of right ribcage boundary candidate points, a series D of left ribcage boundary candidate points, series A+B of upper lung ribcage boundary candidate points, and series C+D of left/right ribcage boundary candidate points.

In the image processing system of FIG. 4, there is provided a digital image inputting apparatus 1 capable of digitizing chest radiographs that were imaged. For digitizing a chest radiograph into a chest image (PA(postero-anterior) chest image), the digital image inputting apparatus 1 serves as an apparatus such as a film digitizer for digitizing a film. For imaging a chest radiograph in digital, the digital image inputting apparatus 1 operates as a digital imaging system such as a CR (computed radiography) system. Either system can be used, provided that it is able to digitize chest films.

An image data storing memory 2 is provided to memorize chest images digitized by the digital image inputting apparatus 1.

A landmark information detector 3, which receives PA chest image data from the digital image inputting apparatus 1, detects information from the PA chest image data the landmark composing part of the ribcage information.

An upper lung ribcage boundary point series detector 4, connected with both landmark information detector 3 and image data storing memory 2, detects upper lung ribcage boundary point series A+B from PA chest image data and landmark information.

A right/left ribcage boundary candidate point series detector 5, connected with the upper lung ribcage boundary point series detector 4, landmark information detector 3, and image data storing memory 2, detects right/left ribcage boundary candidate point series C+D from PA chest image data, information about upper lung ribcage boundary candidate point series, and landmark information.

A curve fitting calculator 6 for upper lung ribcage boundary candidate point series, connected with both upper lung ribcage boundary point series detector 4 and image data storing memory 2, performs curve fitting calculation on the upper lung ribcage boundary point series A+B obtained by the detector 4, thereby providing series of continuously connected points with respect to X-coordinates.

A curve fitting calculator 7 for right/left ribcage boundary candidate point series, connected with both right/left ribcage boundary candidate point series detector 5 and image data storing memory 2, performs curve fitting calculation on the right/left ribcage boundary point series C+D obtained by the detector 5, thereby providing series of continuously connected points with respect to Y-coordinates.

A boundary point series combining unit 8, connected with both curve fitting calculators 6 and 7, combines the upper lung ribcage boundary point series A+B and the right/left ribcage boundary point series C+D on the basis of the landmark information, thereby obtaining a ribcage boundary point series for each of the right and left ribcage.

A ribcage information storing memory 9, which is provided to be connected with both landmark information detector 3 and boundary point series combining unit 8, memorizes the ribcage boundary information obtained by the combining unit 8 and the landmark information detected by the detector 3.

An image displaying processor 10, coupled with the ribcage information storing memory 9 and the image data storing memory 2, performs processing for displaying the ribcage boundary information, chest image data, and others. The processed image data by this processor 10 are then sent to a CRT (cathode ray tube) to visualize an image which can be observed by users.

Other display devices, such as a plasma display or liquid crystal display, can be used instead of the CRT 11. But it is preferable to use the CRT when taking a graduation display performance into account. Moreover, it is preferred that a CRT of which scanning line is more than 1000 in number, which is known as a highly fine CRT for medical diagnosis.

Referring to FIGS. 8 to 12, a method for detecting a ribcage boundary of a digital chest image in the present embodiment will now be described.

In this detection of a ribcage boundary, search starting points to decide ribcage boundaries of right/left lung fields are set to N1 and N2 as shown in FIG. 6. The point N1, which is an intersection made between the lung top line N of a lung and a right lung angle line T, is handled as a search starting point for upper lung right ribcage boundary candidate points. The point N2, which is an intersection made between the lung top line N and a left lung angle line U, is handled as a search starting point for upper lung left ribcage boundary candidate points.

How to decide an inner search limit point and outer search limit point, which will be carried out prior to decision of an upper lung ribcage boundary candidate point series, will now be described.

Figure 8:
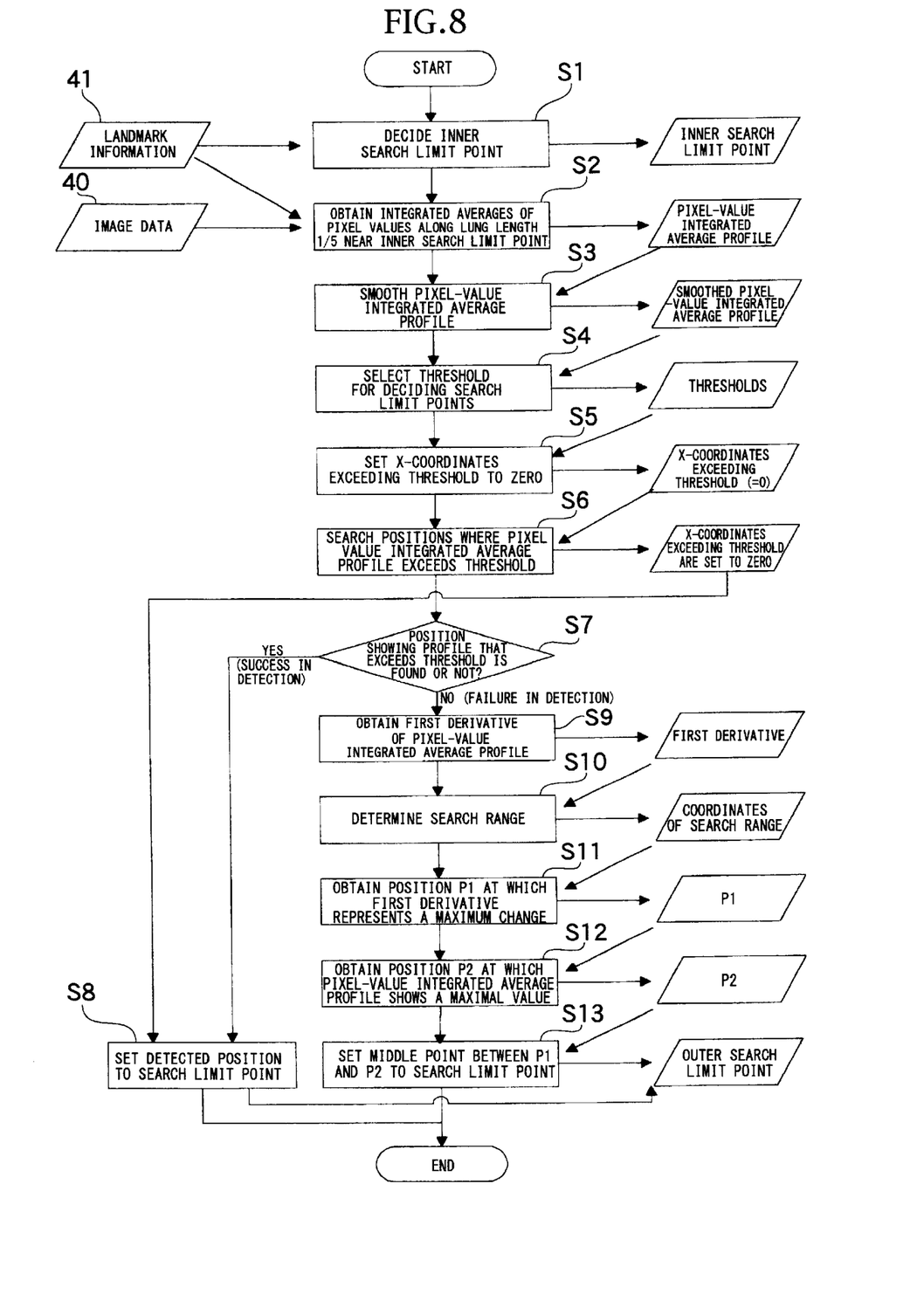
FIG. 8 shows a method of detecting a ribcage boundary from a digital chest image according to the embodiment of the present invention, by using a flowchart, executed prior to decision of series of upper lung ribcage boundary candidate points, for deciding inner search limit points and outer search limit points.

FIG. 8 shows a method for detecting a ribcage boundary of a digital chest image in the present embodiment, in which provided is a flowchart relating to decision of both inner and outer search limit points. This flowchart is executed prior to decision of an upper lung ribcage boundary candidate point series.

At first, based on landmark information 41, an inner search limit point N3 is calculated (Step S1 in FIG. 8). The inner search limit point N3 is expressed, as shown in FIG. 6, by a coordinate of the intersection between lung top line N and midline.

Then, as shown in FIG. 8, based on the landmark information 41 and chest image data 40, integrated averages of pixel values along a lung length ⅕ line are obtained within the width of a chest image (Step S2). In order to reduce noise from a profile of the pixel-value integrated averages obtained at Step S2, the profile date are smoothed (Step S3).

From the smoothed pixel-value integrated average profile, thresholds for deciding the search limit points is selected (Step S4). Of the thresholds, one threshold for deciding a search limit point in the right can be determined by calculating an equation of:

the threshold=a minimum of the smoothed pixel-value integrated average profile in the right lung field+(a maximum of the smoothed pixel-value integrated average profile−a minimum of the smoothed pixel-value integrated average profile in the right/left lung fields)/2.

On the other hand, the other threshold for deciding a search limit point in the left can be determined by calculating an equation of:

the threshold=a minimum of the smoothed pixel-value integrated average profile in the left lung field+(a maximum of the smoothed pixel-value integrated average profile−a minimum of the smoothed pixel-value integrated average profile in the right/left lung fields)/2.

To determine if the search has been made at the next step, X-coordinates exceeding the thresholds are set to zero in advance (Step S5). Then, positions at which the smoothed pixel-value integrated average profile become larger than the threshold are searched in each of the right/left lung fields, respectively, in a manner such that the search is made to advance from centers RM and LM (refer to FIG. 9) of the right and left along the lung length ⅕ line, which are adopted as references, respectively, outwardly in the right/left lung fields (Step S6). The centers RM and LM are positions each showing low pixel value due to a largest amount of X-ray transmission. In the right lung field, the search advances toward a negative direction of the X-coordinates (to the left in FIG. 9), while in the right lung field, the search advances toward the positive direction of the X-coordinates (to the right in FIG. 9).

Figure 10:
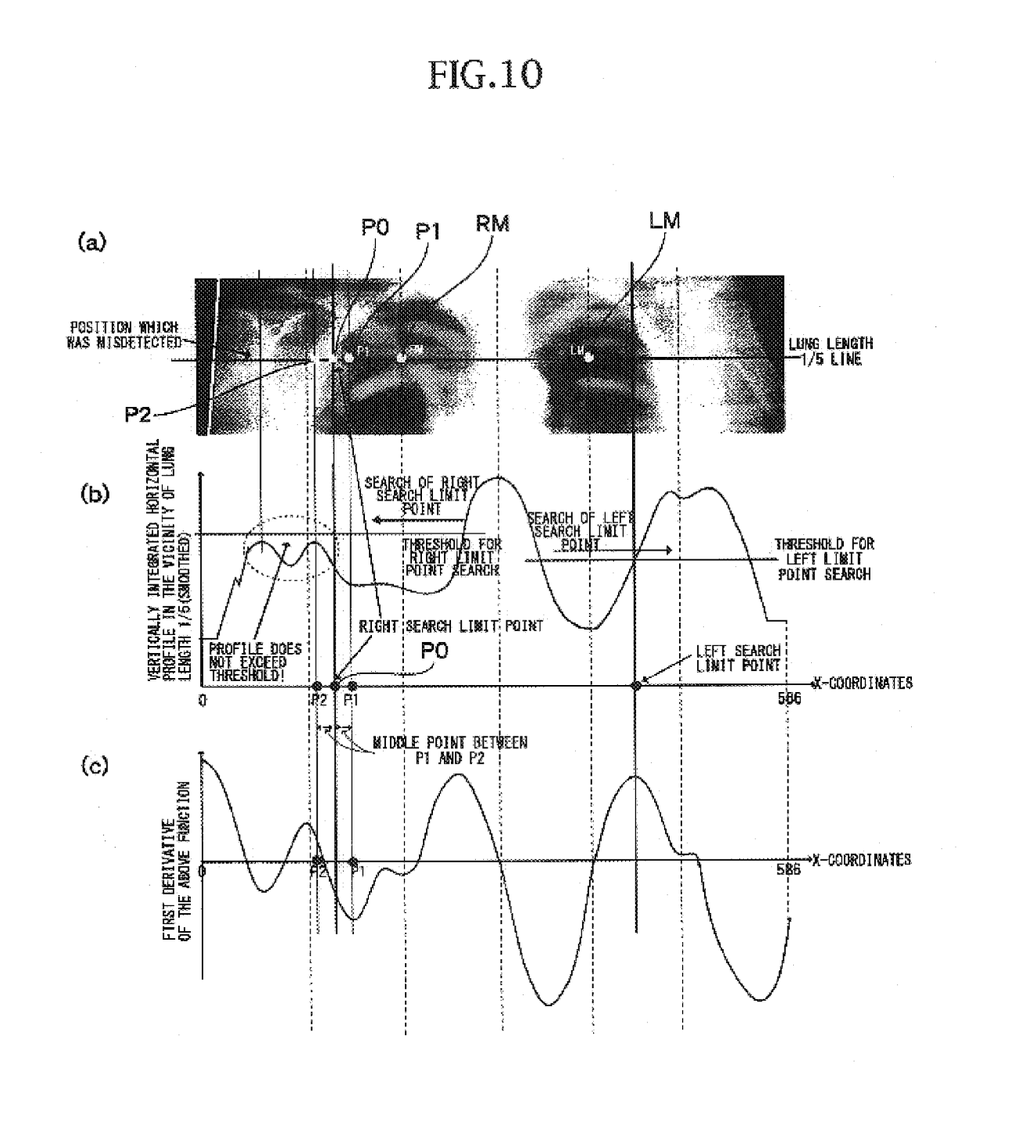
FIG. 10 shows illustrations for outer limit points of upper lung ribcage boundary candidate series in detecting the ribcage boundary, of which part (a) shows a pictorial view of an upper lung, of which part (b) shows a vertically integrated horizontal profile as a lung length ⅕, and of which (c) shows the first derivative of the profile shown in its (b)

During the search, as shown in FIG. 10, it is determined if a position showing the profile that exceeds the threshold is found (Step S7). When such a position is found, the detected position is set to a search limit point (Step S8). But if not found, a first derivative for a smoothed pixel-value integrated average profile obtained field by field at Step S3 is calculated in order to examine changes in pixel value (Step S9).

Figure 9:
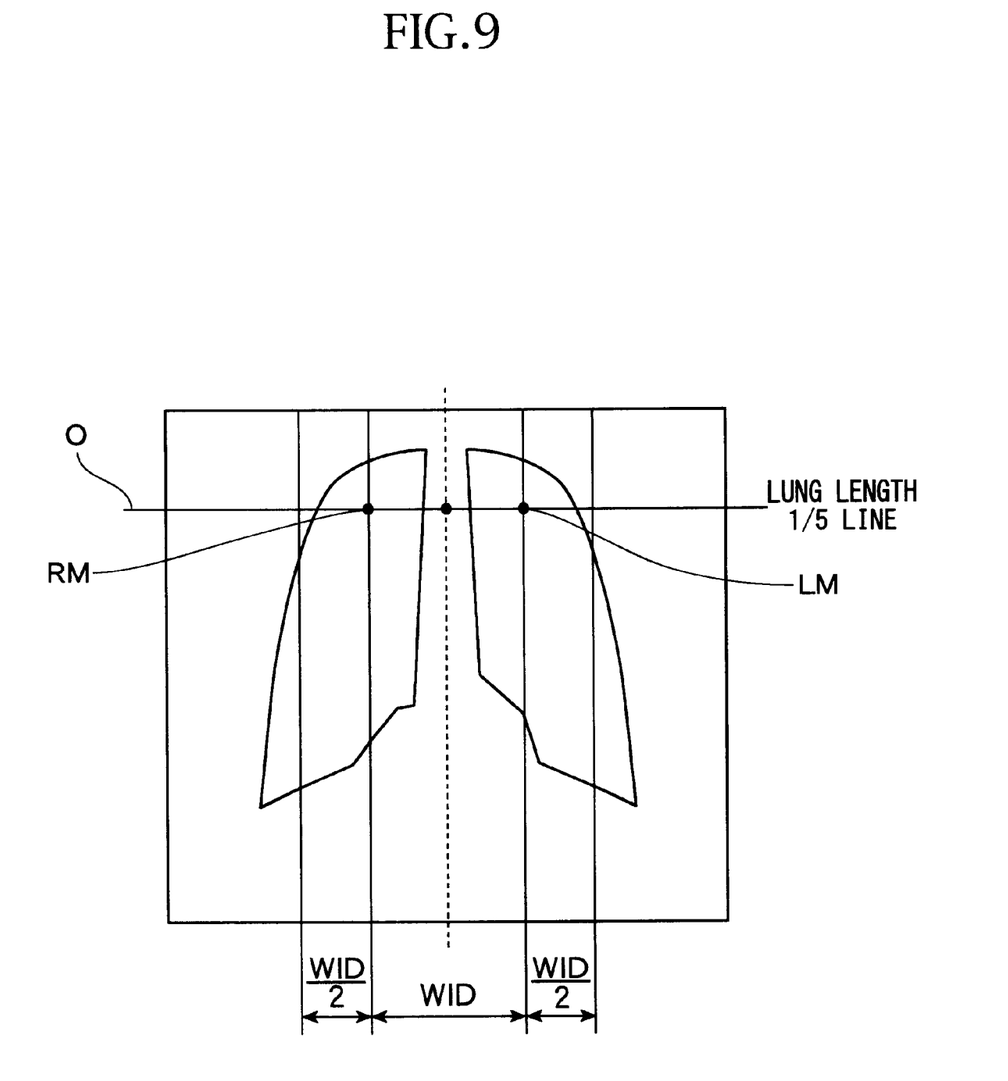
FIG. 9 pictorially shows search ranges of right/left ribcage boundary search limit points in detecting the ribcage boundary.

A search range is then determined (Step S10). In the detection method according to the present embodiment, the search range is set as shown in FIG. 9, field by field, by using the left middle LM (corresponding to J in FIG. 6) and right middle RM (corresponding to H in FIG. 6) as references, the middles being central points (which show a largest amount of X-ray transmission) of the right and left along the lung length ⅕ line. It is enough that both left middle LM and right middle RM are located, respectively, slightly inward from of the center of each of the right and left lung fields. Preferably, both left middle LM and right middle RM are symmetrically located with each other with respect to the midline. When taking a distance from the left middle LM to the right middle as WID, the search range is individually set to WID/2 outwardly in each of the right and left. The lung length ⅕ is approximately located in the vicinity of roots of the clavicles in the lung field. In the present embodiment, the lung length ⅕ is merely one reference employed in deciding the search range, so any reference can be used if it avoids the roots of the clavicles.

Then, a position P1 at which the first derivative represents a maximum change is searched during the search range set at Step S10 (Step S11). This search is made to advance from both of the right middle RM and the left middle LM outwardly in each of the right and left lung fields, as shown in FIG. 10. At the position P1, pixel values normally change from the lung inside to its ribcage boundary.

A position P2 at which each profile of pixel-value integrated averages shows a maximal value is searched during the search range set at Step S10 (Step S12). This search is also made to advance from both of the right middle RM and the left middle LM outwardly in each of the right and left lung fields. The position P2 normally shows the vicinity of a ribcage boundary.

Averages (middle points) of each of the points P1 and P2 detected at Steps S11 and S12 are set to each outer search limit point P0 (Step S13), before this processing is terminated.

FIG. 10 illustrates outer search limit points for the series of upper lung ribcage boundary candidate points. FIG. 10(a) is an pictorial illustration, FIG. 10(b) shows a vertically integrated horizontal profile of the lung length ⅕, and FIG. 10(c) shows a first derivative of the FIG. 10(b). Making comparison among (a) to (c) of FIG. 10 reveals the relationship of P1 described at Step S11, P2 described at Step S12, and P0 descried at Step S13.

As described above, analyzing the positional information of the upper lungnary fields and changes in pixel value within the lung fields leads to detection of the outer search limit points. In this detection method, exceeding a given threshold is not required in deciding the outer search limit points. As a result, even when positions exceeding a given threshold cannot be searched, as in the case that a region of clavicles or scapulas of which contrast is low, the outer search limit points can correctly be set in the vicinity of the ribcage boundary.

A method for deciding points to start search of the right/left ribcage boundary candidate point series on the basis of the right and left middles, which is executed before deciding the right and left ribcage boundary candidate point series, will now be described.

In the case of the conventionally used technique, the X-coordinate of an boundary candidate point located at the outermost position (i.e., a position showing an X-coordinate of a lowest value) within a right lung field was obtained from an upper right ribcage boundary candidate point series, so that a search starting point for a right ribcage boundary candidate point series was decided thereat. On the other hand, the X-coordinate of an boundary candidate point located at the outermost position (i.e., a position showing an X-coordinate of a largest value) within a left lung field was obtained from an upper left ribcage boundary candidate point series, so that a search starting point for a left ribcage boundary candidate point series was decided thereat.

Figure 11:
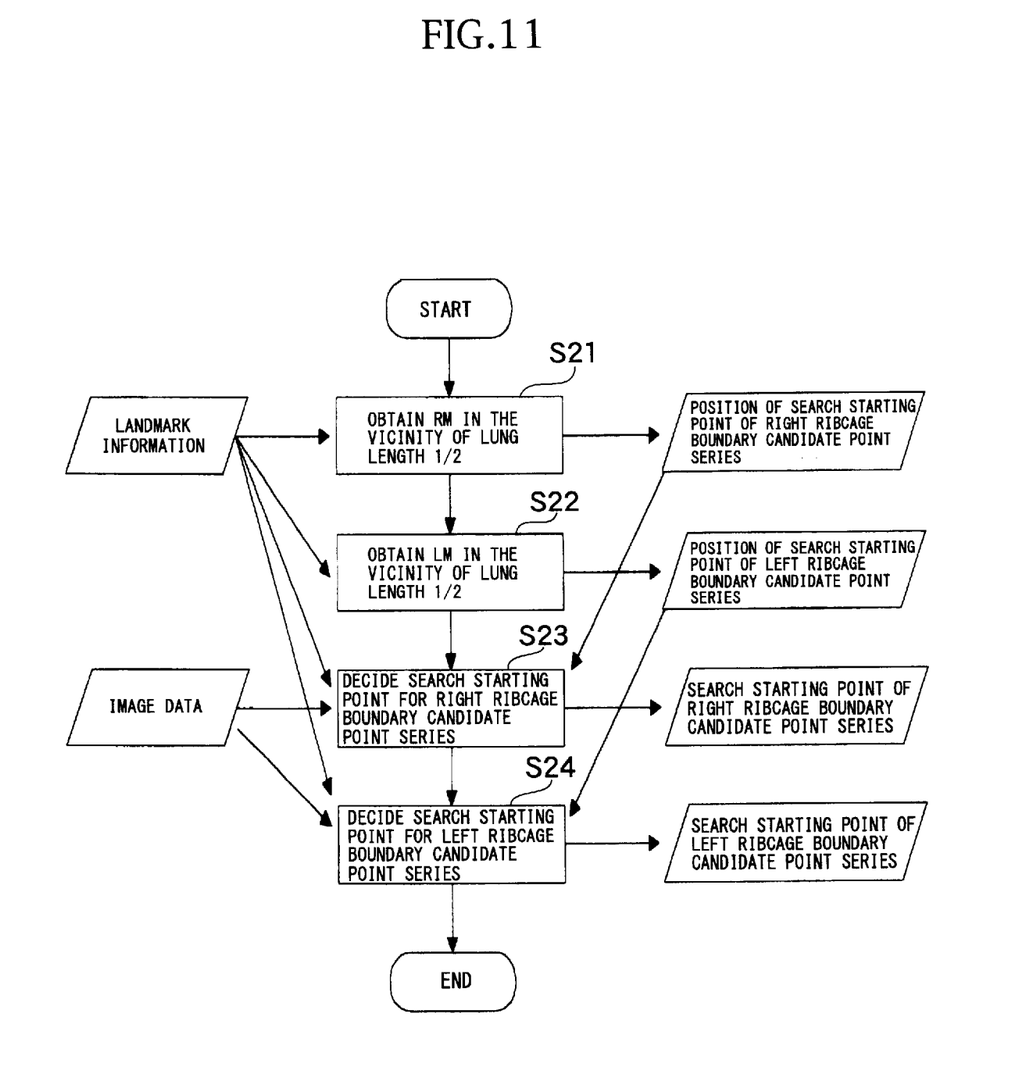
FIG. 11 is a flowchart showing decision of start points of right/left ribcage boundary candidate point series, which also explains the ribcage boundary detection.

In contrast, in the ribcage boundary detection on a digital chest image according to the present embodiment, search starting points for the right and left ribcage boundary candidate point series are decided, as shown in a flowchart of FIG. 11, without using information about the upper-right and upper-left ribcage boundary candidate point series.

At first, the coordinate of a right middle RM on the lung length ½ (i.e., the position K in FIG. 6) is acquired from the landmark information (Step S21). The coordinate of a left middle LM on the lung length ½ (i.e., the position M in FIG. 6) is then acquired from the landmark information (Step S22). The coordinate of the right middle RM is then decided as a search starting point for the series of right ribcage boundary candidate points (Step S23), before the coordinate of the left middle LM is decided as a search starting point for the series of left ribcage boundary candidate points (Step S24). After this, the processing is terminated. In those procedures, the processing orders can be exchanged between the right and left.

In the present embodiment, the middles RM and LM on the lung length ½ line are symmetric in the right and left about the midline (symmetry axis) and located inward compared to the central positions of the right and left lung fields, respectively. Alternatively, if the middles RM and LM are located such that they reside in the vicinity of the central positions of the right and left lung fields and are as symmetric about the midline as possible, slight deviations from the symmetry between the middles are allowable.

An experiment conducted by the present inventors revealed that a few percentage of the failures in detection of ribcage boundaries resulted from failures in detection of upper right and left ribcage boundaries. Therefore, in cases detecting the right and left ribcage boundaries on a chest image is resulted in failure owing to the fact that detection failed in the upper lung ribcage boundary, such detection will succeed by employing the ribcage boundary detection technique of digital chest images according to the present invention.

A method for deciding search starting points for right and left ribcage boundary candidate point series will now be described. The method, which is included in the ribcage boundary detection method of the present invention, is realized by processing executed prior to decision of the series of right and left ribcage boundary candidate points. The method has a feature of removing artifacts in deciding the search starting points.

In the case of the conventional technique, as shown in FIG. 2, a blank 49 which occurs in conversion into a digital image by use of a film digitizer and/or artifacts such as black regions 50 which occur in image processing are included in its original image. This inclusion prevents the search starting point from being obtained correctly, thus sometimes failing in detecting the search limit point for detecting the series of ribcage boundary candidate points.

Considering this drawback, the present invention adopts the ribcage boundary detection by which artifacts that appear in a circumferential end portion of a chest image due to its profile are removed. This removal will lead to correct decision of search starting points for the right and left ribcage boundary candidate points.

Figure 12:
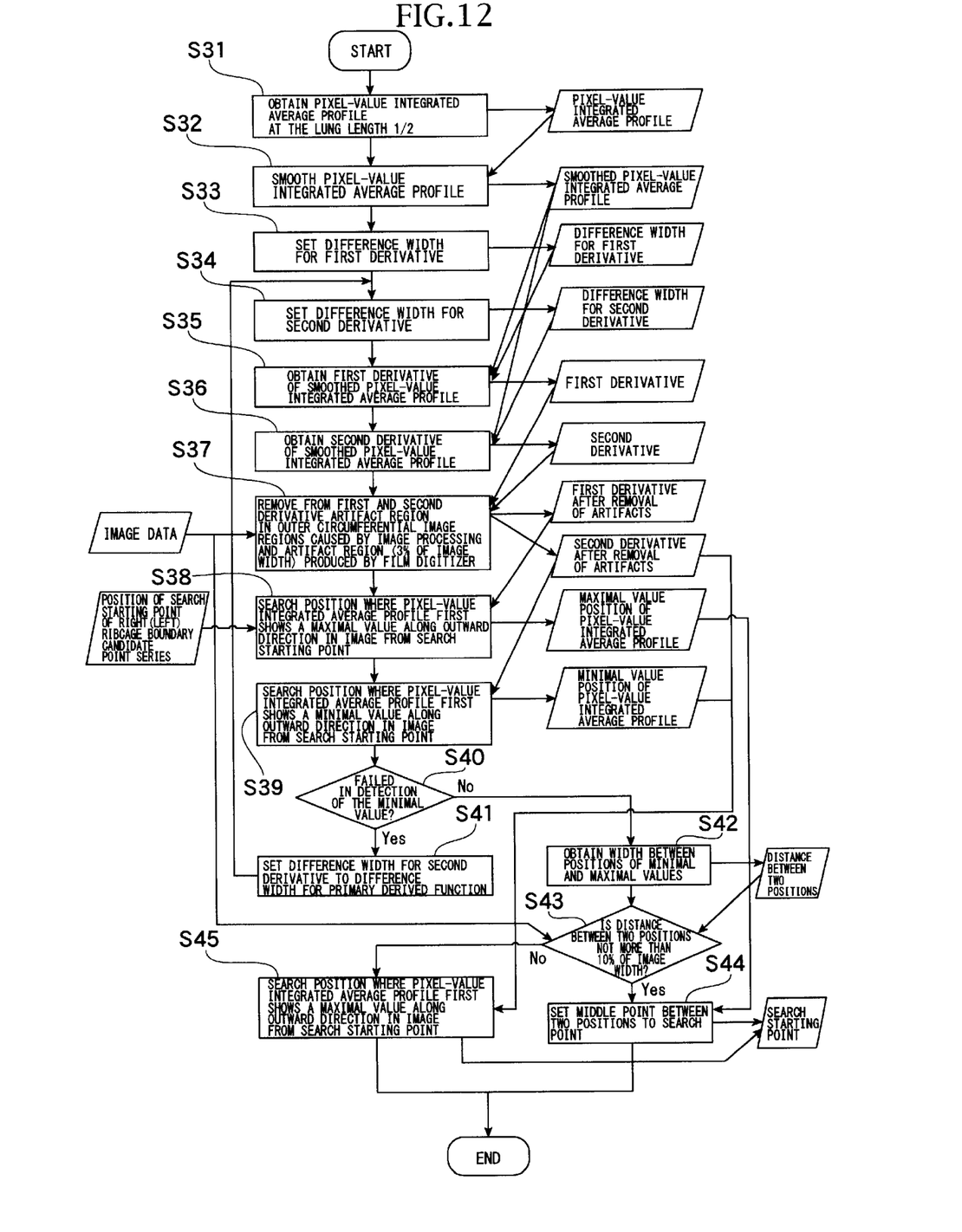
FIG. 12 is a flowchart showing decision of start points of right/left ribcage boundary candidate point series, which also explains the ribcage boundary detection.

According to a flowchart shown in FIG. 12, more practical procedures will now be described.

First, vertical pixel-value integrated averages at the lung length ½ line in an image width of a chest image are acquired (Step S31). In order to lower noise of a profile of the vertical pixel-value integrated averages acquired at Step S31, the profile is smoothed (Step S32). A difference width used for obtaining a first derivative of the smoothed pixel-value integrated average profile obtained at Step S32 is set (Step S33). In the present embodiment, the difference width is set to 2% of the image width. Alternatively, the difference width may be set to the extent necessary to allow gentle changes in the pixel-value integrated average profile.

Then, from the difference width set at Step S33, a difference width for obtaining a second derivative is set (Step S34). By way of example, in the present invention, such a difference width is set to 4% of the image width. Alternatively, the difference width may be set to the extent necessary to allow gentle changes in the pixel-value integrated average profile. Additionally, it is preferred to assign a larger amount to such a difference width than that set at Step S33.

Using the difference width set at Step S33, a first derivative of the smoothed pixel-value integrated average profile is then calculated (Step S35). Successively, using the difference width set at Step S34, a second derivative of the smoothed pixel-value integrated average profile is then calculated (Step S36).

Then, an effective search range is determined such that blanks produced in conversion into a digital image by use of a film digitizer and/or artifacts appearing in outer circumferential regions of a chest image during image processing are removed from the first and second derivative (Step S37).

In the case of the present embodiment, the width of a longitudinal band that is caused when general film digitizers are used was about 2.1% of the image width (approximately, 12 pixels). Accordingly, design was made in a manner that, with taking a safety factor based on this figure into account, a width of 3% was removed across-the-board from the image width. Alternatively, in accordance with characteristics of a film digitizer which is actually used and/or a technique of image processing to be performed, a desired width may be selected.

Then, based on the first derivative calculated at Step S35 and the effective search range decided at Step S37, the smoothed pixel-value integrated average profile undergoes search from its search start position along an outward direction of the chest image, during which search a position first showing a maximal value is detected as a searched position (Step S38). Similarly, based on the second derivative calculated at Step S36, the smoothed pixel-value integrated average profile undergoes search from its search start position along an outward direction of the chest image, during which search a position first showing a minimal value is detected as a searched position (Step S39).

It is then determined if the minimal value can be detected (Step S40). If the minimal value could not be detected, the difference width for the second derivative is shortened to a smaller amount than the present width (for example, to a difference width which has been set for the first derivative) (Step S41), before returning to Step S34. Although the difference width for the second derivative is set to that for the first derivative in the present embodiment, it is not limited to such a difference width. The difference width for the second derivative may be set to the extent that changes in the second derivative can be detected.

If the minimal value can be detected, a difference in the positions calculated at Steps S38 and S39 (an absolute value corresponding to a distance between the pixels) is calculated, thereby a width between positions showing the minimal and maximal values being provided (Step S42).

Then, it is determined whether the distance between the two positions is not more than 10% of the image width (Step S43). When the distance is not more than 10% of the image width, a middle point between the two positions (i.e., an averaged position between the two positions showing the maximal and minimal values) is set to a search starting point (Step S44). By contrast, when the distance is over 10% of the image width, the position that represented the maximal value for the first time is set to a search starting point (Step S45), then the processing is terminated. Though the threshold is assigned to 10% in the present embodiment, it is not confined to such an amount. Another example is to assign the threshold to an appropriate value in relation to a size of the lungs and an image size.

Such processes are able to provide preprocessing that removes artifacts, such as a blank 49 to be caused during a conversion into a digital image by use of a film digitizer and/or noises 50 to be caused in image processing, unlike seen in FIG. 2. Because the detection of the search starting point is not influenced by such artifacts, the ribcage boundary information can be obtained with precision without depending on quality of chest images that have been given.

The ribcage boundary detection method for digital chest images according to the embodiment of the present invention can be applied to computer-aided diagnosis that has been used, in which lesion-enhanced images are used to detect temporal changes of lung diseases between or among digital chest images imaged at different times for the same patient. Additionally, this ribcage boundary detection method can be applied to computer-aided diagnosis that is not directed to a plurality of images. For instance, after detecting anatomical structure information on the chest from a single chest image, the resulting anatomical structure information can be image-processed by computer-aided diagnosis that uses the ribcage boundary detection method of the present invention.

Although the description above contains many specifities, these should not be construed as limiting the scope of the invention but as merely providing illustrations of some of the presently preferred embodiments of the present invention. Thus the scope of the present invention should be determined by the appended claims and their equivalents.

What we claim is:

1. A system for detecting a ribcage boundary for computer-aided diagnosis requiring anatomical structure information to be detected from a digital chest image, comprising:

means for obtaining a horizontal profile of smoothed pixel-value integrated averages in each of right and left lung fields of the image in the vicinity of ⅕ lung length;

means for deciding a threshold for each of the right and left lung fields with each of the horizontal profiles taken as a reference;

means for searching each of the right and left lung fields from a central part of each lung field outwardly on the digital chest image so as to determine a position exceeding each of the thresholds when the position being set as an outer search limit point for a series of upper lung ribcage boundary candidate points for a ribcage boundary;

means for calculating a first derivative of the horizontal profile for examining changes in pixel value within each of the right and left lung fields in cases when the position exceeding each of the thresholds is not found; and means for searching not only a position from the central part of each of the right and left lung fields outwardly on the digital chest image within a predetermined search range, the position showing a maximum change in the first derivative, but also a position showing a maximal value in the horizontal profile within the search range for each of the right and left lung fields; and means for deciding a median between the maximal value and the position showing a maximum change in the first derivative as the outer search limit point for each of the right and left lung fields.

2. A method for detecting a ribcage boundary for computer-aided diagnosis requiring anatomical structure information to be detected from a digital chest image, comprising the steps of:

obtaining a horizontal profile of smoothed pixel-value integrated averages in each of right and left lung fields of the image in the vicinity of ⅕ lung length;

deciding a threshold for each of the right and left lung fields with each of the horizontal profiles taken as a reference;

searching each of the right and left lung fields from a central part of each lung field outwardly on the digital chest image so as to determine a position exceeding each of the thresholds when the position being set as an outer search limit point for a series of upper lung ribcage boundary candidate points for a ribcage boundary;

calculating a first derivative of the horizontal profile for examining changes in pixel value within each of the right and left lung fields in cases when the position exceeding each of the thresholds is not found; and searching not only a position from the central part of each of the right and left lung fields outwardly on the digital chest image within a predetermined search range, the position showing a maximum change in the first derivative, but also a position showing a maximal value in the horizontal profile within the search range for each of the right and left lung fields; and deciding a median between the maximal value and the position showing a maximum change in the first derivative as the outer search limit point for each of the right and left lung fields.

3. A method for detecting a ribcage boundary for computer-aided diagnosis requiring anatomical structure information to be detected from a digital chest image, comprising the steps of:

setting a central position in each of right and left lung fields on the chest image, the central position being in the vicinity of a lung length of ½, the central position in each field being symmetric right and left with regard to a midline regarded as a symmetric axis; and deciding a search starting point for each of series of right and left ribcage boundary candidate points from a central position of each of the right and left lung fields outwardly on the chest image.

4. The method of claim 3, wherein the deciding step includes a step of performing pre-processing for removing an artifact including at least one of a blank arising during a conversion into the digital chest image by use of a film digitizer and a noise caused by image processing performed on the chest image.

* * * * *